(12) United States Patent
Case et al.

(10) Patent No.: US 7,527,643 B2
(45) Date of Patent: May 5, 2009

(54) EXCHANGEABLE DELIVERY SYSTEM FOR EXPANDABLE PROSTHETIC DEVICES

(75) Inventors: Brain C. Case, Bloomington, IN (US); Charles W. Agnew, West Lafayette, IN (US); Ram H. Paul, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 629 days.

(21) Appl. No.: 11/139,930

(22) Filed: May 27, 2005

(65) Prior Publication Data

US 2005/0267563 A1    Dec. 1, 2005

Related U.S. Application Data

(60) Provisional application No. 60/575,475, filed on May 28, 2004.

(51) Int. Cl.
*A61F 2/06* (2006.01)
(52) U.S. Cl. .................................................... 623/1.11
(58) Field of Classification Search ............... 623/1.11, 623/1.12
See application file for complete search history.

(56) References Cited

U.S. PATENT DOCUMENTS

| | | | |
|---|---|---|---|
| 4,762,129 A | 8/1988 | Bonzel | |
| 5,591,194 A | 1/1997 | Berthiaume et al. | |
| 5,772,669 A * | 6/1998 | Vrba | 623/1.11 |
| 6,200,336 B1 | 3/2001 | Pavcnik et al. | |
| 7,175,650 B2 * | 2/2007 | Ruetsch | 623/1.12 |
| 7,309,350 B2 * | 12/2007 | Landreville et al. | 623/1.11 |
| 2003/0109886 A1 | 6/2003 | Keegan et al. | |
| 2004/0064067 A1 | 4/2004 | Ward | |
| 2004/0073230 A1 | 4/2004 | Mulholland et al. | |

FOREIGN PATENT DOCUMENTS

WO    WO 03/003944 A    1/2003

* cited by examiner

*Primary Examiner*—Todd E Manahan
*Assistant Examiner*—Eric Blatt
(74) *Attorney, Agent, or Firm*—Buchanan Intellectual Property Office LLC (57) ABSTRACT

Exchangeable delivery systems, methods of making delivery systems, and methods of delivering a self-expandable prosthetic device are provided. Delivery systems according to embodiments of the invention include an elongate tubular member defining a passageway with a distal end defining an exchange port, and a distal tip member slideably disposed partially within the distal end of the passageway.

13 Claims, 10 Drawing Sheets

EXCHANGEABLE DELIVERY SYSTEM FOR EXPANDABLE PROSTHETIC DEVICES

CROSS REFERENCE TO RELATED APPLICATION

This application claims priority to U.S. Provisional Application Ser. No. 60/575,475 filed on May 28, 2004 the entire disclosure of which is hereby incorporated into this disclosure in its entirety.

FIELD OF THE INVENTION

The invention relates to delivery systems for placement of expandable prosthetic devices within a body vessel.

BACKGROUND OF THE INVENTION

Minimally invasive medicine, the practice of gaining access to a body vessel, duct, or organ using a wireguide to facilitate the subsequent introduction of other medical devices, has been evolving since the Seldinger technique was first popularized during the late 1950s and 1960s. The ability to exchange medical devices over a single indwelling wireguide without requiring displacement of the wireguide from the treatment site provided a significant advance. Using an "over the wire" exchange technique, a user could remove one medical device from the treatment site and advance another medical device to the site without losing access to the site provided by the wireguide. This technique provided greater control over positioning of medical devices and introduced efficiencies to minimally invasive treatment techniques.

"Over the wire" exchange techniques require the use of long wireguides because the user must be able to maintain control of the wireguide, independent of the device over the wireguide, at all times during an exchange. As a result, extremely long wireguides are typically used. For most techniques, a wireguide with a length that is at least double the length of the device being placed over the wire is used. These long wireguides may be viewed as cumbersome by some users.

The development of rapid exchange delivery systems and techniques allowed the use of shorter wireguides. In these systems, the wireguide and medical device, such as a catheter, are coupled to each other only along a portion of the length of the medical device. The wireguide exits a passageway of the medical device at a point between the proximal and distal end of the medical device via a port formed in a wall of the device. This allows the user to control the proximal end of the wireguide while removing a medical device placed along the wireguide. During removal, the coupled portion of the wireguide travels along the length of the wireguide, ultimately exiting the patient. At this point, the user can exchange medical devices by simply pulling the proximal end of the wireguide through the relatively short wireguide lumen of the device, and subsequently pass the proximal end of the wireguide through the wireguide lumen of a second medical device. Finally, the second device is advanced along the wireguide to the point of treatment. During the exchange, the wireguide position within the body vessel is maintained even though a relatively short length of wireguide extends outside of the patient.

Rapid exchange delivery systems and techniques have proven particularly desirable in coronary medicine where it is common for a sequence of procedures using multiple catheter-based devices to be performed over a single wireguide. For example, it is common to place multiple balloon-expandable stents in a body vessel following angioplasty. Rapid exchange delivery systems and techniques allow the placement of multiple stents without requiring withdrawal and replacement of the wireguide and without requiring the use of relatively long wireguides.

Self-expandable prosthetic devices are frequently used in a variety of treatment procedures. For example, prosthetic devices are frequently used in a variety of treatment procedures. For example, self-expandable stents are used to provide support to various vessels and ducts in the gastrointestinal system. Also, some prosthetic valves, including prosthetic venous valves, include a self-expandable support frame. In some circumstances, it may be desirable to place multiple self-expandable prosthetic devices in one or more body vessels using a single wireguide.

Accordingly, there is a need for improvements in exchangeable delivery systems and methods for expandable prosthetic devices.

SUMMARY OF EXEMPLARY EMBODIMENTS OF THE INVENTION

The invention provides delivery systems for placing self-expandable prosthetic devices within a body vessel. In one exemplary embodiment, a delivery system according to the invention comprises an elongate tubular member defining a passageway extending between proximal and distal ends. A distal tip member defines a second passageway extending between its proximal and distal ends. The proximal end of the distal tip member defines a proximal surface and is slideably disposed within the passageway of the elongate tubular member. A pusher is disposed within the passageway of the elongate tubular member and is adapted to interact with the proximal surface of the distal tip member. The delivery system also includes a means for retaining the proximal end of the distal tip member within the passageway of the elongate tubular member.

The invention also provides methods of making delivery systems. The invention also provides methods of placing one or more self-expandable prosthetic devices within a body lumen. The methods of placing can include an exchange of one delivery system or component thereof for another on a previously placed wireguide. The methods of placing can be used to place multiple self-expandable prosthetic devices within a body vessel at one or more points of treatment. In one exemplary embodiment of the invention, one delivery system is exchanged for another over a previously placed wireguide to place multiple prosthetic valves within a vein of a patient.

The reader can gain additional understanding of the invention by reviewing the following description of exemplary embodiments of the invention with reference to the appended drawings.

DETAILED DESCRIPTION OF EXEMPLARY EMBODIMENTS OF THE INVENTION

The following detailed description and the appended drawings are provided to describe and illustrate exemplary embodiments of the invention for the purpose of enabling one of ordinary skill in the relevant art to make and use the invention. The description and drawings are not intended to limit the scope of the invention or its protection in any manner.

FIGS. 1 through 4 illustrate a delivery system 10 according to a first exemplary embodiment of the invention. The delivery system 10 includes an elongate tubular member 12, a distal tip member 14, a pusher 16, and a means for retaining a proximal portion of the distal tip member 14 within the tubular member 12. In the embodiment illustrated in FIGS. 1 through 4, the means for retaining comprises a cap member 18 disposed on the tubular member 12.

The tubular member 12 can be any suitable tubular member, such as a sheath formed of plastic or other suitable material. Other examples of suitable tubular members include introducers, guiding catheters, and endoscopes. The tubular member has inner 22 and outer 24 surfaces and defines a passageway 26 extending from a proximal end 28 to a distal end 30. The passageway 26 provides a space within which other components of the delivery system 10 can be disposed. The proximal end 28 can include any desirable connectors and/or adaptors, such as a threaded fitting 32, Touhy-Borst adapter, and other suitable connectors and adaptors. Also, a handle or handle system configured to allow sliding of the pusher 16 relative to the tubular member 12, or vice versa, could be attached to the proximal end 28 of the tubular member 12. These elements, however, are not required, and the tubular member 12 can indeed comprise a simple tubular body.

Figure 2:
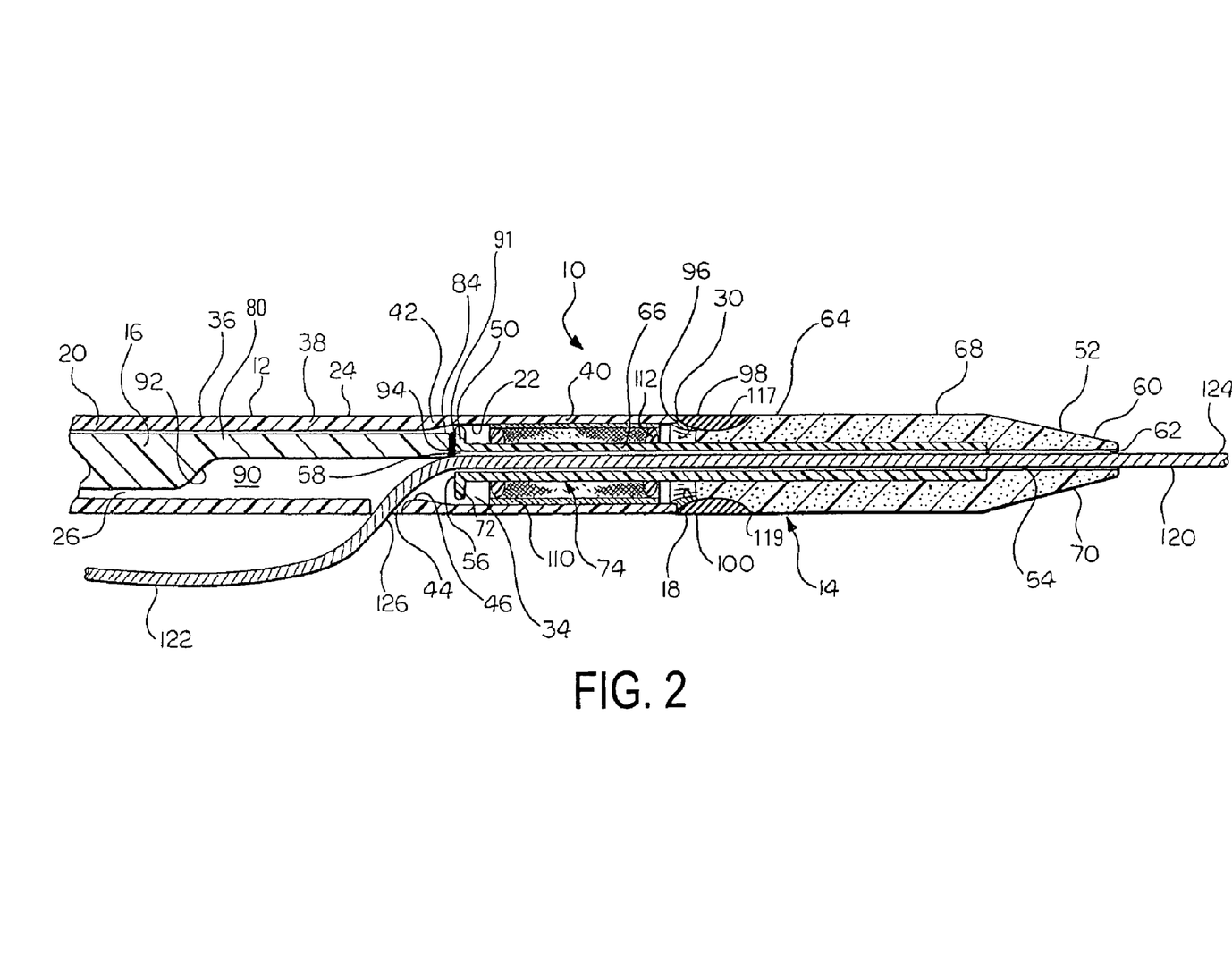
FIG. 2 is a sectional view of the delivery system illustrated in FIG. 1 disposed on a wireguide with an expandable prosthetic device.

The tubular member 12 defines a distal cavity 34 that receives a portion of the distal tip member 14. In the illustrated embodiment, the distal cavity 34 is a portion of and is continuous with the passageway 26. The inner diameter of the tubular member 12 at the distal cavity 34 is larger than the inner diameter of the tubular member 12 at at least one other portion of the tubular member 12, such as at a portion proximal to the distal cavity 34. In the illustrated embodiment, the enlarged inner diameter of the tubular member 12 at the distal cavity 34 is formed by a relatively thin wall thickness of the tubular member 12. As best illustrated in FIG. 2, the wall 36 of the tubular member 12 includes a first portion 38 having a first wall thickness and a second portion 40 having a second wall thickness. The second wall thickness is less than the first wall thickness. A transition region 42 of the wall 36 is disposed between the first 38 and second 40 portions of the wall 36, and includes a wall thickness that varies from the first wall thickness to the second wall thickness. As will be described more fully below, this configuration of the tubular member is advantageous at least because it provides a desired distal cavity 34 for receiving a portion of the distal tip member 14 and the transition region 42 provides a means for limiting axial movement of the distal tip member 14 within the passageway 26.

As will be described more fully below, the tubular member 12 defines an exchange port 44 through which a wireguide 120 can be passed. As used herein, the term "wireguide" refers to elongate members used in minimally invasive procedures to define a path along which other devices can be advanced. In this context, the term is considered equivalent to the term "guidewire". The exchange port 44 provides a communicative passageway between the passageway 26 defined by the tubular member 12 and the external environment of the tubular member 12. The exchange port 44 comprises an opening through the wall 36 of the tubular member 12. The exchange port can have any suitable size and configuration, and the specific size and configuration chosen for any particular embodiment of the invention will depend on several factors, including the diameter(s) of any wireguide(s) with which a particular delivery system will be used. As best illustrated in FIG. 2, the wall 36 of the tubular member can define a rounded edge 46 on the distal side of the exchange port 44. The rounded edge 46 facilitates movement of the delivery system 10 over the wireguide 120.

The distal tip member 14 provides a structure for carrying an expandable prosthetic device 110. In the illustrated embodiment, the distal tip member 14 comprises a separate member from the tubular member 12. The distal tip member 14 has proximal 50 and distal 52 ends and defines a passageway 54 extending between the ends 50, 52. The passageway 54 is adapted to receive a portion of a wireguide 120, and can have any suitable size and configuration. The specific size and configuration chosen for any particular embodiment of the invention will depend on several considerations, including the diameter(s) of any wireguide(s) with which a particular delivery system will be used.

As described more fully below, the distal tip member 14 provides a proximal surface 56 at the proximal end 50 that is able to interact with a surface 94 of the pusher 16. An opening 58 is defined at the proximal end 50 and provides access to the passageway 54. The distal end 52 provides a tapered surface 60 and defines an opening 62 that also provides access to the passageway 54. The tapered surface 60 provides a smaller profile to the distal end 52 of the distal tip member 14, which facilitates navigation of the delivery system 10 through body vessels.

In the illustrated embodiment, the distal tip member 14 comprises a tip body 64 and a tubular member 66. As best illustrated in FIG. 2, the tip body 64 and tubular member 66 can comprise separate members. These two portions of the distal tip member 14 can also be integrally formed as a unitary structure. In the illustrated embodiment, the tip body 64 includes a main body 68 and a tapered portion 70. The main body is a substantially cylindrical portion and advantageously has an outer diameter that is slightly larger than the outer diameter of the tubular member 12, although this is not required. The tapered portion 70 provides the desirable tapered surface 60. The tubular member 66 defines a flange 72 that provides the desired surface 56 for interaction with the pusher 16 of the delivery system 10. As best illustrated in FIG. 2, the outer diameter of the flange 72 is advantageously sized to be slightly less than the inner diameter of the tubular member 12 at the distal cavity 34 and slightly greater than the inner diameter of the tubular member 12 at a portion proximal to the transition region 42. This configuration of the flange 72 is advantageous at least because it provides the desired surface 56 for interaction with the pusher 16 and it acts to limit axial movement of the distal tip member 14 within the passageway 26 of the tubular member 12. The flange 72 can be integrally formed with the tubular member 66 of the distal tip member 14, or can comprise a separately attached member. It is noted that the pusher 16 can interact with the proximal surface 56 of the distal tip member at any point or points on the surface 56, including points on the periphery of the surface 56 as well as centrally-located points.

The distal tip member 14 defines a mounting region 74 on which a self-expandable prosthetic device can be disposed. The mounting region 74 is a portion of the distal tip member 14 that is able to receive an expandable prosthetic device 110 and need not have any particular structural features. In the embodiment illustrated in FIG. 2, the mounting region 74 comprises a portion of an external surface of the tubular member 66 disposed between the flange 72 and the proximal end of the tip body 64.

Two or more self-expandable prosthetic devices could also be disposed on the mounting region 74. Furthermore, the distal tip member 14 could be configured to define multiple mounting regions, either continuous with or discreet from the other mounting region(s). Delivery systems according to these embodiments could be used to deploy multiple self-expandable prosthetic devices. The pusher 16 or another component could be configured to provide information relating to the deployment status of one or more of the multiple self-expandable prosthetic devices.

The distal tip member 14 can be formed of any suitable material or materials, and the specific material or materials chosen will depend on several considerations, including the intended application of the delivery system 10. In the embodiment illustrated in FIGS. 1 through 4, the tip body 64 is formed of a flexible polymeric material, such as polyurethane. Any suitable pliant material can be used to form the tip body, including flexible polymers, gels, and similar materials. The tubular member 66 is formed from a relatively hard plastic or other polymeric material, and the tip body 64 is disposed on the tubular member 66. The flange 72 of this embodiment is integrally formed by the tubular member 66.

Figure 1:
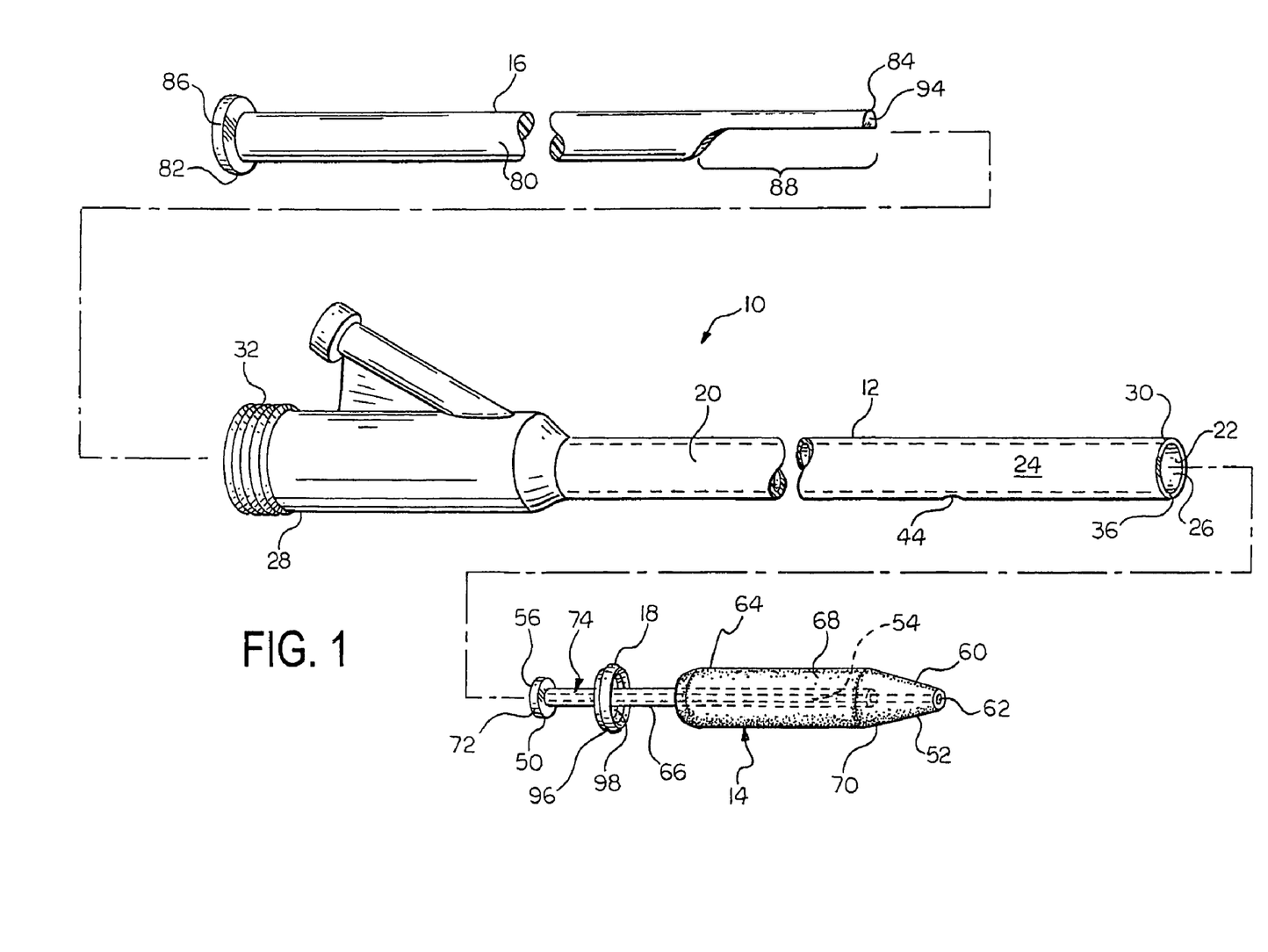
FIG. 1 is an exploded perspective view of a delivery system according to a first exemplary embodiment of the invention.
Figure 4:
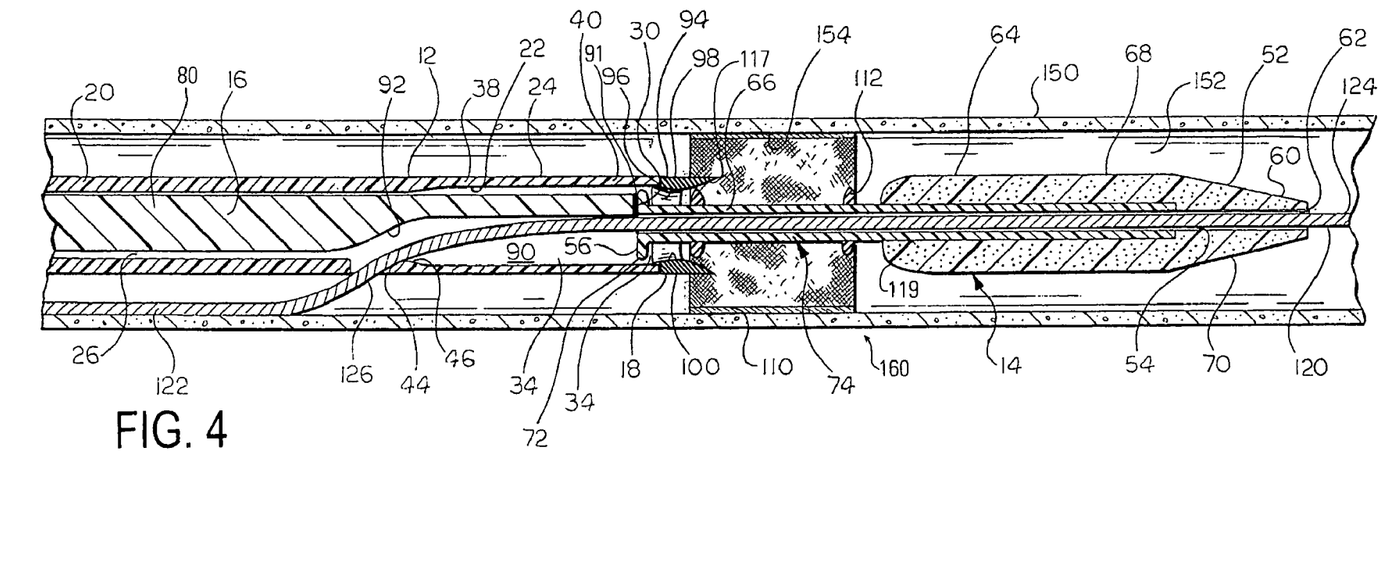
FIG. 4 is a sectioned partial view of a body vessel containing the delivery system illustrated in FIG. 1 disposed on a wireguide with an expandable prosthetic device in a fully deployed configuration.

The pusher 16 is an elongate member adapted to be substantially disposed within the passageway 26 of the tubular member 12. The pusher 16 comprises a main body 80 and has proximal 82 and distal 84 ends. A flange 86 or other structure can be disposed at the proximal end 82 to provide a connector, adapter, or to limit axial movement of the pusher 16 within the passageway 26 of the tubular member 12. As best illustrated in FIG. 1, the pusher 16 of this embodiment includes a distal portion 88 having a reduced width as compared to that of the main body 80. As best illustrated in FIG. 2, this reduced width at the distal portion 88 creates a void region 90 when the pusher 16 is disposed in the passageway 26 of the tubular member 12. The pusher 16 of the illustrated embodiment includes ogee 92 that transitions the width of the pusher between the larger and smaller widths and partially defines the void region 90 within the tubular member 12. As best illustrated in FIG. 4, the void region 90 can accommodate a portion of a wireguide 120 as the pusher 16 is advanced axially toward the distal end 30 of the tubular member 12.

The distal end 84 of the pusher 16 defines a pushing surface 94 adapted to transfer a force generated by axial movement of the pusher 16 within the passageway 26 of the tubular member 12 onto the proximal surface 56 of the distal tip member 14. The pushing surface 94 advantageously lies in a plane that is substantially parallel to a plane in which the proximal surface 56 of the distal tip member 14 lies. The pushing surface 94 can have any suitable size and configuration, including the semi-circular configuration illustrated in FIGS. 1 through 4. Also, the pusher 16, as best illustrated in FIG. 2, can be attached to the proximal end 50 of the distal tip member 14, such as by an adhesive, weld, or other suitable means 91 for attaching two members. Alternatively, the pusher 16 and the distal tip member 14 can comprise separate, non-attached members. Attachment of these two members, while optional, is considered advantageous at least because it prevents complete escape of the distal tip member 14 from the tubular member 12.

The pusher 16 can be formed of any suitable material, including plastics and other polymeric materials, and metals. Furthermore, the pusher 16 can include other structural features as desired. For example, it may be advantageous to form the pusher 16 to include a lumen that provides communication to the passageway 26 of the tubular member 12. Also, the pusher 16 can have any suitable structure that allows it to accommodate a portion of a wireguide 120 disposed within the tubular member 12. For example, a pusher with a substantially uniform width could be used. In this embodiment, one or more sufficiently stiff wires or other members could be made to project outward from a distal end of the pusher. The wires could be used to interact with the proximal surface 56 of the distal tip member 14 while still accommodating a portion of a wireguide.

The delivery system 10 includes a means for retaining a proximal portion of the distal tip member 14 within the tubular member 12. Any suitable means can be used, and a variety of suitable structures are described herein. In the embodiment illustrated in FIGS. 1 through 4, the means for retaining a proximal portion of the distal tip member 14 within the tubular member 12 comprises a cap member 18 disposed on the distal end 30 of the tubular member 12. The cap member 18 is a ring-like structure defining a recess 96 and an opening 98. The recess 96 is adapted to substantially receive a portion of the wall 36 of the tubular member 12. The opening 98 is sized and configured to permit passage of a first portion of the distal tip member 14 and prevent passage of a second portion of the distal tip member 14. For example, as best illustrated in FIG. 2, the opening 98 of the cap member 18 in the exemplary embodiment is sized and configured to permit through passage of the tubular member 66 of the distal tip member 14 and to prevent through passage of the tip body 64. Also; as described more fully below, the opening 98 is sized and configured to prevent through passage of the flange 72.

The cap member 18 defines an interior surface. This surface 13 can be disposed at an angle to the inner surface 22 of the tubular member 12. Any suitable angle can be used, and the specific angle chosen for a particular embodiment will depend on several considerations, including the type of self-expandable prosthetic device with which the delivery system is intended to be used. The angle should be sufficient to provide the desired means for retaining a proximal portion of the distal tip member 14 within the tubular member 12. An angle that places the interior surface in a position relative to the inner surface 22 that does not significantly interfere with passage of the expandable prosthetic device 110 from the passageway 26 of the tubular member 12 to the environment external to the tubular member 12 is desirable.

The cap member 18 can be formed of any suitable material, including plastic and other polymeric materials. It may be advantageous to form the cap member 18 of the same material as the tubular member 12 as this may provide desirable attachment properties between these two structures. The cap member 18 could also be formed of metals and other radiopaque materials. These materials may be advantageous in embodiments for which visibility is desired during use, such as under fluoroscopy during treatment techniques. The cap member 18 is attached to the distal end 30 of the tubular member 12, and can be attached by any suitable means for attaching two members together, including adhesives, threaded and other mated fittings, and structural connectors such as rivets. Also, various attachment techniques, such as welding and melt-forming, can be used.

As best illustrated in FIG. 2, the distal interior surface 117 of the cap member 18 is complimentary to a proximal shoulder 119 of the tip body 64. This advantageously provides a proximal shoulder 117 to the tip body 64 that facilitates withdrawal of the delivery device 10 following deployment of the prosthetic device 110. During the withdrawal process, the tip body 64 must pass through, or at least near, the prosthetic device 110. The proximal shoulder is considered advantageous at least because it substantially eliminates a surface edge that may engage the prosthetic device 110 during withdrawal.

Figure 3:
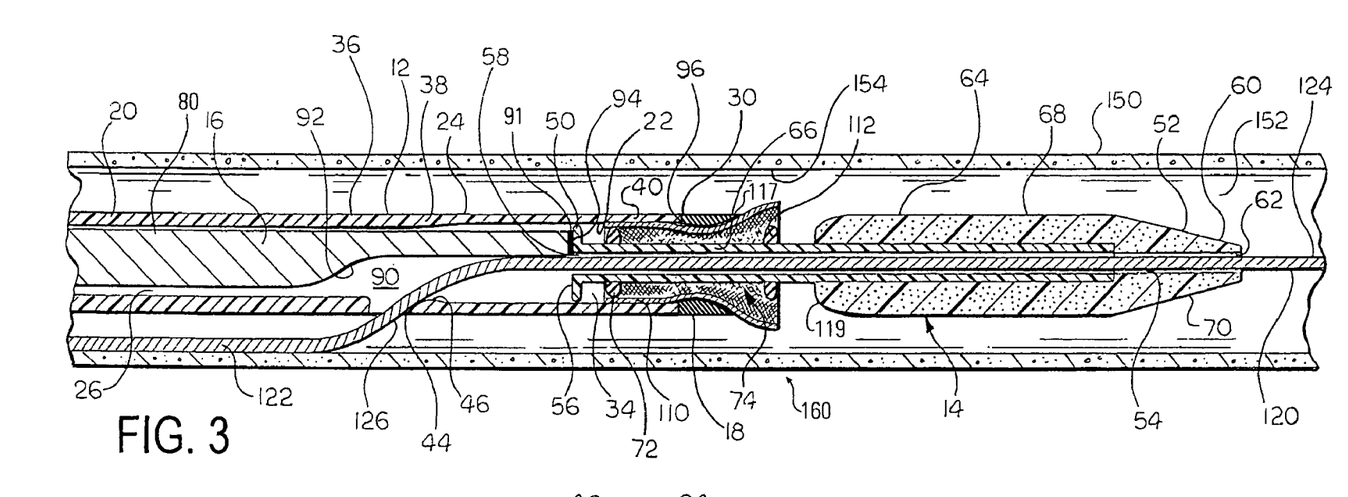
FIG. 3 is a sectioned partial view of a body vessel containing the delivery system illustrated in FIG. 1 disposed on a wireguide with an expandable prosthetic device in a partially deployed configuration.

Delivery systems according to the invention are particularly well suited for use in deployment of self-expandable prosthetic devices. Accordingly, a self-expandable prosthetic device can be disposed on the mounting region 74 of the distal tip member 14. Any suitable type of self-expandable prosthetic device can be used with the delivery systems according to the invention, including self-expandable stents, prosthetic valves that include a self-expandable support frame, such as prosthetic valves for implantation in a vein (prosthetic venous valves), self-expandable filters, distal protection devices, vessel occluders, and other self-expandable devices. Suitable self-expandable prosthetic devices for use with delivery systems according to the invention include those described in U.S. Pat. No. 6,200,336 to Pavcnik et al. for a MULTIPLE-SIDED INTRALUMINAL MEDICAL DEVICE; United States Application for patent Ser. No. 10/642,372 of Pavcnik et al. for an IMPLANTABLE VASCULAR DEVICE, filed on Aug. 15, 2003; and United States Application for patent Ser. No. 10/828,716 of Case et al. for an ARTIFICIAL VALVE PROSTHESIS WITH IMPROVED FLOW DYNAMICS, filed on Apr. 21, 2004; the entire disclosures of which are hereby incorporated into this disclosure for the purpose of describing suitable self-expandable prosthetic devices for use with delivery systems according to the invention. FIGS. 2 through 4 illustrate the delivery system 10 according to the first exemplary embodiment with a self-expandable prosthetic device 110 disposed on the mounting region 74 of the tubular member 66 of the distal tip member 14. The illustrated self-expandable prosthetic device 110 is a self-expandable stent, but it is expressly contemplated by the inventors that this device 110 is exemplary in nature.

A self-expandable prosthetic device 110 will tend to expand within the passageway 26 of the tubular member 12 when the device 110 is disposed on the passageway 26. To ensure that such a device 110 advances with the distal tip member 14 when the pusher 16 advances the distal tip member 14, a means for temporarily securing the prosthetic device 110 to the distal tip member 14 can be used. Any suitable structure and/or composition can be used as the means for temporarily securing the prosthetic device 110 to the distal tip member 14. The specific structure/composition chosen should secure the prosthetic device 110 so it advances within the passageway 26 upon advance of the distal tip member 14, but should release the prosthetic device 110 upon its exiting of the passageway 26, as best illustrated in FIG. 3. In the embodiment illustrated in FIGS. 2 through 4, two adhesive bands 112 are used as the means for temporarily securing the prosthetic device 110 to the distal tip member 14. Alternatively, the proximal end of the prosthetic device 110 can be butted against the distal surface of the proximal end 50 of the distal tip member 14. Also alternatively, both a means for temporarily securing and an abutting positioning can be employed.

FIG. 2 illustrates the delivery system 10 according to the first embodiment disposed on a wireguide 120. The wireguide 120 is known in the art and will not be described in detail herein. Briefly, the wireguide 120 includes a proximal portion 122, a distal portion 124, and an intermediate portion 126 disposed between the proximal 122 and distal 124 portions. The delivery system 10 is disposed on the wireguide 120 by passing an end of the wireguide 120 through an opening of the delivery system 10, such as the opening 62 of the distal tip member 14, and into the passageway 26 of the tubular member 12. The wireguide 120 exits the passageway 26 by passing through the exchange port 44. Delivery systems according to the invention are adapted for efficient exchanges for other delivery systems over a previously placed wireguide. Accordingly, during use of the delivery systems according to the invention, only a portion of a wireguide 120 is disposed in a portion of the length of the passageway 26 of the tubular member 12.

FIGS. 3 and 4 illustrate the delivery system 10 according to the first embodiment during two stages of deployment of an included self-expandable prosthetic device 110. In FIG. 3, the self-expandable prosthetic device 110 is partially deployed. In FIG. 4, the self-expandable prosthetic device 110 is fully deployed. A review of FIGS. 3 and 4 demonstrates the functioning of the delivery system 10 according to the first embodiment of the invention.

In both FIGS. 3 and 4, the delivery system 10 is disposed on a wireguide 120 that has been previously placed in a body vessel 150. The wireguide 120 extends through the lumen 152 of the body vessel 150, and can be placed according to techniques known in the art. The delivery system 10 has been advanced over the wireguide 120 and moved along the wireguide 120 to a desired point of treatment 154 in the body vessel 150. As illustrated in FIGS. 3 and 4, the distal end of the wireguide 120 is typically advanced beyond the point of treatment 154 prior to deployment of the self-expandable prosthetic device 110. The delivery system 10 is then advanced over the wireguide 120 until the distal end 160 is at or near the point of treatment 154. Once the delivery system 10 is properly positioned, the pusher 16 is moved axially toward the distal end 30 of the tubular member 12. This axial movement of the pusher 16 results in axial movement of the distal tip member 14 due to interaction between the pushing surface 94 of the pusher 16 and the proximal surface 56 of the distal tip member 14. With continued axial movement of the pusher 16 and the resulting axial movement of the distal tip member 14, the self-expandable prosthetic device 110 advances through the opening 98 of the cap member 18. The self-expandable prosthetic device 110 may deflect inward as it moves along the interior surface 100 of the cap member 18. As the self-expandable prosthetic device 110 exits the opening 98 of the cap member 18, the device 110 is released from the adhesive bands 112 and expands within the lumen 152 of the body vessel 150. FIG. 3 illustrates the self-expandable prosthetic device 110 in a partially deployed state.

The self-expandable prosthetic device 110 can also be deployed by retracting the tubular member 12 over the pusher 16 while substantially maintaining the position of the pusher 16. The retraction of the tubular member 12 gradually reveals the mounting region 74, resulting in deployment of the self-expandable prosthetic device 110.

Once the distal tip member 14 has been advanced to a sufficient degree, the self-expandable prosthetic device 110 completely exits the opening 98 of the cap member 18. At this point, the self-expandable prosthetic device 110 is free to expand along its entire length within the lumen 152 of the body vessel 150. FIG. 4 illustrates the self-expandable prosthetic device 110 in a fully deployed state.

In this embodiment, the cap member 18 retains a proximal portion of the distal tip member 14 within the tubular member 12. Specifically, in this embodiment, the flange 72 of the distal tip member 14 is prevented from passing through the opening 98 of the cap member 18 because the outer diameter of the flange 72 is larger than the inner diameter of the opening 98.

Following deployment of the self-expandable prosthetic device 110, the delivery system 10 is withdrawn from the body vessel 150. Withdrawal can be accomplished in a variety of manners. For example, the entire assembly, including the wireguide 120, can be withdrawn as a single unit. This may be desirable if it is known that there is no need to pass another delivery system over the wireguide 120. If, however, it may be necessary to pass another delivery system over the wireguide 120 and the delivery system 10, the user can withdrawal the delivery system 10 while leaving the wireguide 120 in its position within the body vessel 150. To accomplish this, the user fixes the wireguide 120 in position relative to the body vessel 150, such as by holding the wireguide 120 with a hand or attaching a proximal portion of the wireguide 120 to the patient, e.g., taping the wireguide 120 to the skin of the patient. Also, a locking device that fixes the wireguide in position relative to the body vessel can be used. Once the position of the wireguide 120 is fixed, the user can withdraw the delivery system 10 while leaving the wireguide 120 in place. The user pulls on a proximal portion of the delivery system 10, which causes the delivery system 10 to retract along the wireguide 120. As the delivery system 10 retracts, the intermediate portion 126 of the wireguide 120 moves through the exchange port 44 of the tubular member 12, through the distal cavity 34, through the passageway 54 of the distal tip member 14, and through the opening 62 at the distal end 52 of the distal tip member 14. Eventually, the proximal end (not illustrated in the Figures) of the wireguide 120 passes through the delivery system 10 in the same manner as the intermediate portion 126 and exits the opening 62 at the distal end 52 of the distal tip member 14. At this point, the delivery system 10 is free of the wireguide 120, and the wireguide 120 has remained in position within the lumen 152 of the body vessel 150. Another delivery system can then be advanced along the wireguide 120 to the same or a different point of treatment in the body vessel 150.

Another technique can be used to withdraw the delivery system 10 while leaving the wireguide 120 in place. In this alternative technique, the position of the wireguide 120 is fixed relative to the body vessel 150, as in the exchange technique described above. Next, the delivery system 10 is advanced distally over the wireguide 120 so that the distal end (not illustrated in the Figures) of the wireguide 112 enters the opening 62 at the distal end 52 of the distal tip member 14. The delivery system 10 is further advanced distally within the lumen 152 of the body vessel 150 so that the distal end of the wireguide 120 passes through the passageway 54 of the distal tip member 14, through the distal cavity 34 of the tubular member 12, and exits the exchange port 44. At this point, the delivery system 10 is free of the wireguide 120 and can be completely withdrawn from the body vessel 150. The wireguide 120 has remained in position within the lumen 152 of the body vessel 150. Another delivery system can then be advanced along the wireguide 112 to the same or a different point of treatment in the body vessel 150. Alternatively, the delivery system 10 can be maintained in substantially the same position while the wireguide 120 is retracted until the distal end of the wireguide 120 exits the exchange port 44. Also, a combination of advancing the delivery system 10 and retracting the wireguide 120 can be used. These exchange techniques, which can be referred to as intravascular or intraductal exchange, intravascular or intraductal uncoupling, and/or remote uncoupling, are described in United States Provisional Application for Patent Ser. No. 60/575,656, filed on May 13, 2004, and entitled SYSTEM AND METHOD FOR INTRODUCING MULTIPLE MEDICAL DEVICES, the entire disclosure of which is hereby incorporated by reference herein for the purpose of describing this exchange technique.

Embodiments of the invention for use in intraductal exchange techniques advantageously include at least one marker at or near the exchange port 44. The marker should be visible under conventional visualization techniques appropriate for the intended procedure in which the delivery system 10 will be used, such as a marker visible under fluoroscopy. A circumferential marker disposed around the edge of the exchange port 44 is advantageous, as are spot and longitudinal markers disposed on or adjacent the edge of the exchange port 44. Delivery devices according to these embodiments can be used with a wireguide that includes a marker at its distal end. This pairing allows a user to determine the point in time during the intraductal exchange procedure at which the wireguide has exited the exchange port 44, which indicates the point in time at which it is appropriate to begin withdrawal of the delivery device 10. Alternatively, a wireguide having an entire distal end that is radiopaque can be used. Furthermore, the proximal end of the tubular member 12 can include indicia that, in conjunction with indicia on a wireguide used with the tubular member 12, provide information relating to the relative positions of the distal ends of the tubular member 12 and wireguides. These indicia can be useful in determining the point at which the delivery system 10 and wireguide have been uncoupled from each other.

Figure 5:
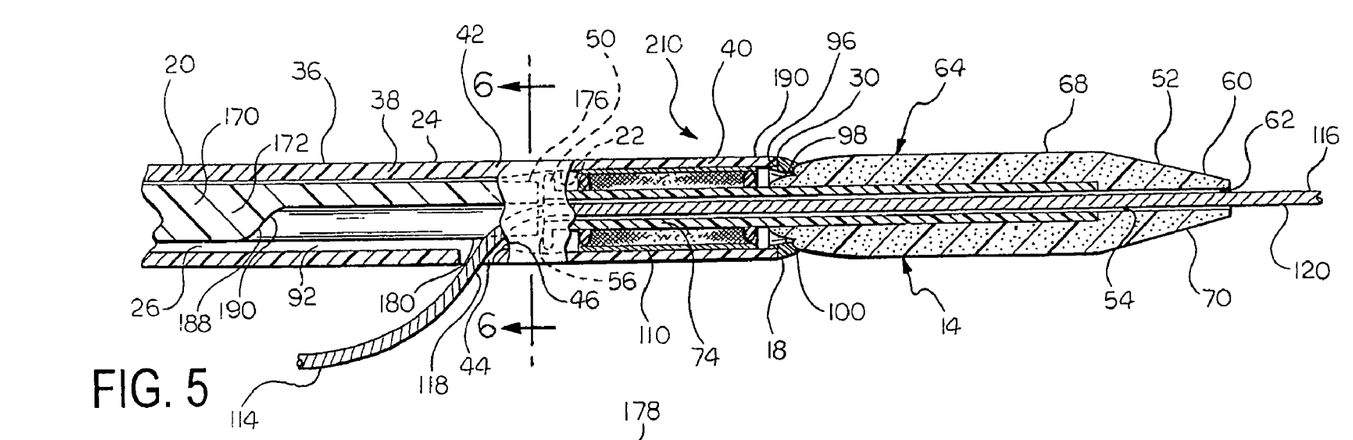
FIG. 5 is a sectional view of a delivery system according to a second exemplary embodiment of the invention.
Figure 6:
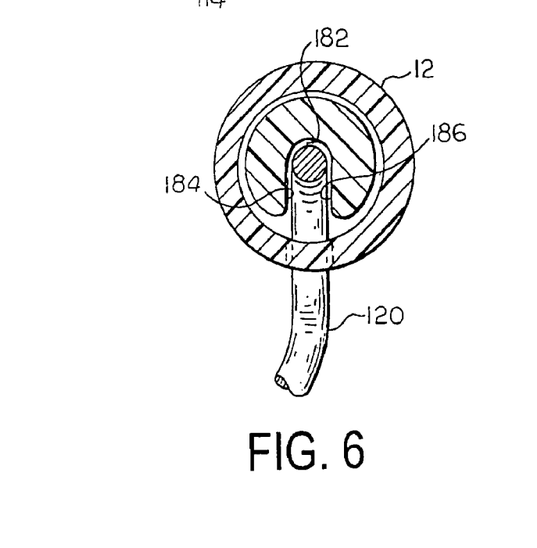
FIG. 6 is a magnified cross-sectional view of the delivery system illustrated in FIG. 5, taken along line 6-6.

FIGS. 5 and 6 illustrate a delivery system 210 according to a second exemplary embodiment of the invention. The delivery system 210 according to this embodiment of the invention includes the tubular member 12, distal tip member 14, and cap member 18 according to the first exemplary embodiment.

Accordingly, reference numbers in FIGS. 5 and 6 for these elements refer to similar features and/or components described above in conjunction with FIGS. 1 through 4.

Figure 7:
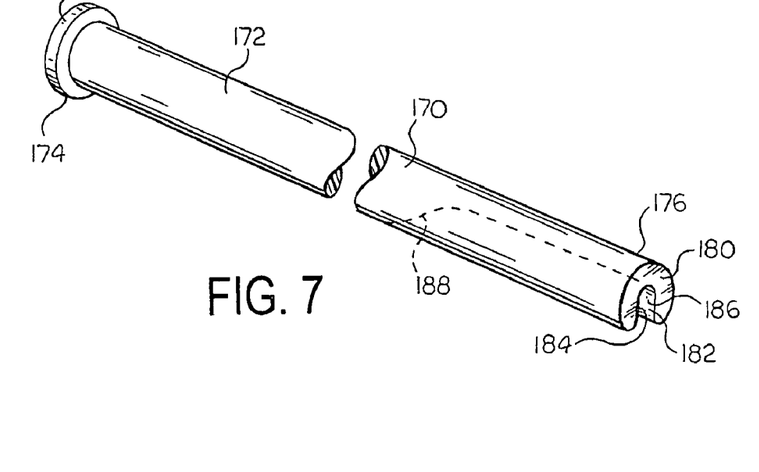
FIG. 7 is a perspective view of the pusher of the delivery system illustrated in FIG. 5.

In this embodiment, the delivery system 210 includes a pusher 170 having a main body 172, a proximal end (not illustrated in FIGS. 5 and 6), and a distal end 176. FIG. 7 illustrates the pusher 170 of this embodiment free of the remaining components of the delivery system 210. The proximal end 174 includes a flange 178 having an increased diameter as compared to that of the main body 172. The distal end 176 provides a pushing surface 180 and defines a channel 182. The channel 182 is defined by first 184 and second 186 opposing surfaces and a proximal end surface 188, and is sized and configured to receive a portion of a wireguide 120 placed within the delivery system 210. Any suitable configuration can be used for the channel 182. The illustrated U-shaped configuration is exemplary only. The channel 182 advantageously has a length that is substantially the same as or at least slightly greater than the distance between the proximal surface 56 of the distal tip member 14 and the proximal side of the exchange port 44 of the tubular member 12 when the distal tip member 14 is fully advanced distally within the tubular member 12. This length for the channel 182 allows the channel 182 to receive the length of the wireguide 120 that will be within the passageway 26 of the tubular member 12 while the distal tip member 14 is fully advanced distally within the tubular member 12. Also advantageously, the proximal end surface 188 is curvilinear, such as the ogee 190 illustrated in FIG. 5. This configuration is believed to avoid kinking or other alterations to the wireguide 120 when the pusher 170 is fully advanced distally within the tubular member 12.

As the pusher 170 is advanced distally within the passageway 26 of the tubular member 12, the channel 182 receives an increasing length of the wireguide 120. The pusher 170 advances the distal tip member 14 in a similar manner as described above for the first exemplary embodiment.

Figures 8, 9:
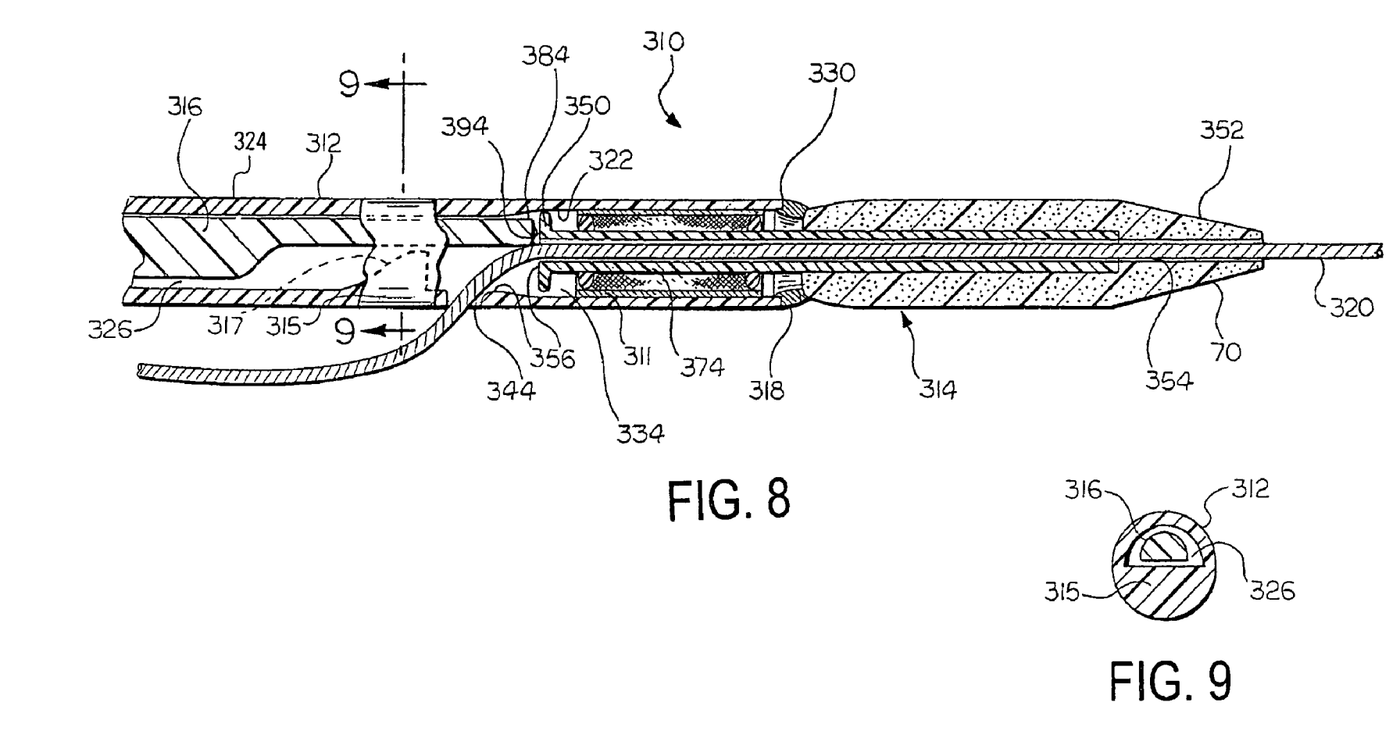
FIG. 8 is a sectional view of the delivery system according to a third exemplary embodiment of the invention.
FIG. 9 is a cross-sectional view of the delivery system illustrated on FIG. 8, taken along line 9-9.

FIGS. 8 and 9 illustrate a delivery system 310 according to a third exemplary embodiment of the invention. The delivery system according to this embodiment is similar to the embodiment illustrated in FIGS. 1 through 4, except as indicated below. Accordingly, the delivery system 310 includes an elongate tubular member 312, a distal tip member 314, a pusher 316, and a means for retaining a proximal portion of the distal tip member 314 within the tubular member 312. Similar to the embodiment illustrated in FIGS. 1 through 4, the means for retaining comprises a cap member 318 disposed on the tubular member 312.

The tubular member 312 has inner 322 and outer 324 surfaces and defines a passageway 326 extending from a proximal end (not illustrated in FIGS. 8 and 9) to a distal end 330. The tubular member 312 defines a distal cavity 334 and an exchange port 344 through which a wireguide 320 can be passed.

The distal tip member 314 is a separate member from the tubular member 312, and has proximal 350 and distal 352 ends and defines a passageway 354 extending between the ends 350, 352. The passageway 354 can receive a portion of the wireguide 320. The distal tip member 314 defines a mounting region 374 on which an expandable medical device 311 can be disposed.

The distal tip member 314 provides a proximal surface 356 at the proximal end 350 that is able to interact with a pushing surface 394 of the pusher 316.

In this embodiment, the tubular member 312 includes a projection 315 disposed in the passageway 326. As best illustrated in FIG. 9, the projection 315 can be defined by the tubular member 312. Alternatively, a separate member could be attached to the tubular member 312 to form a projection. The projection 315 defines a ramp 317 that forces the pusher 316 into an appropriate position within the passageway 326 of the tubular member 312 as the pusher 316 is axially advanced over the projection 315. As best illustrated in FIG. 8, the projection 315 forces the distal end 384 of the pusher 316 to a position substantially opposite the exchange port 344. This positioning limits contact between the pusher 316 and the wireguide 320 within the passageway 316 of the tubular member 312.

Figure 10:
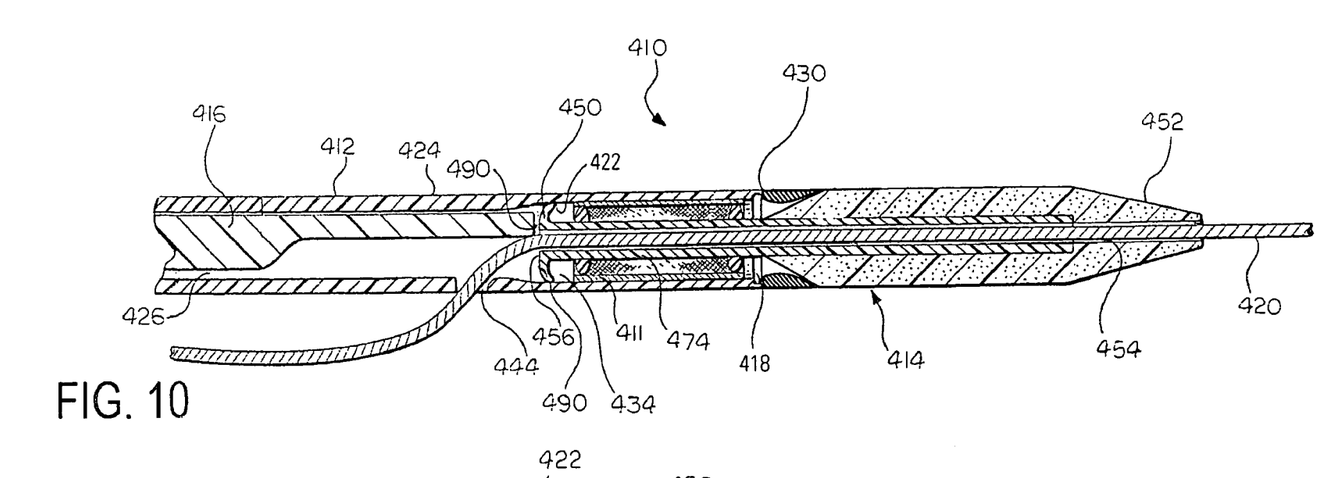
FIG. 10 is a sectional view of the delivery system according to a fourth exemplary embodiment of the invention.
Figure 11:
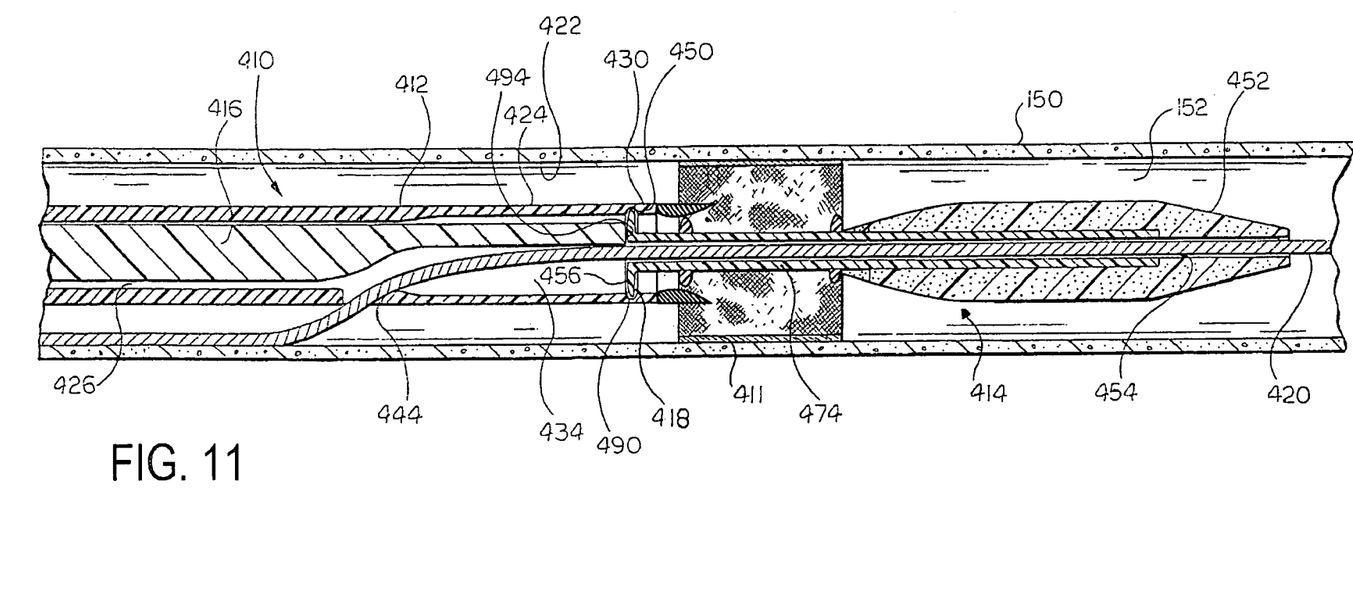
FIG. 11 is a sectioned partial view of a body vessel containing the delivery system illustrated in FIG. 10 disposed on a wireguide with an expandable prosthetic device in a fully deployed configuration.

FIGS. 10 and 11 illustrate a delivery system 410 according to a fourth exemplary embodiment of the invention. The delivery system 410 of this embodiment is similar to the embodiment illustrated in FIGS. 1 through 4, except as indicated below. Accordingly, the delivery system 410 includes an elongate tubular member 412, a distal tip member 414, a pusher 416, and a means for retaining a proximal portion of the distal tip member 414 within the tubular member 412. In this embodiment, the means for retaining comprises an indent 418 in the inner surface 422 of the tubular member 412.

The tubular member 412 has inner 422 and outer 424 surfaces and defines a passageway 426 extending from a proximal end (not illustrated in FIGS. 10 and 11) to a distal end 430. The tubular member 412 defines a distal cavity 434 and an exchange port 444 through which a wireguide 420 can be passed.

The distal tip member 414 is a separate member from the tubular member 412, and has proximal 450 and distal 452 ends and defines a passageway 454 extending between the ends 450, 452. The passageway 454 can receive a portion of a wireguide 420. The distal tip member 414 defines a mounting region 474 on which a self-expandable medical device 411 can be disposed.

The distal tip member 414 provides a proximal surface 456 at the proximal end 450 that is able to interact with a pushing surface 494 of the pusher 416. In this exemplary embodiment, the proximal surface 456 of the distal tip member 414 comprises a flexible member. The flexible member can be integrally formed with the remainder of the distal tip member, or can comprise a separately attached member. For example, in the illustrated embodiment, the proximal surface 456 comprises a flexible section of material that is attached to a proximal end of a tubular member 466. The flexible member can have any suitable size and configuration. The flexible member advantageously includes one or more outer portions that are sized and configured to become disposed within the indent 418 of the tubular member 412 when the proximal end 450 of the distal tip member 414 is disposed substantially adjacent the indent 418 within the tubular member 412. Further, the flexible member can be formed of any suitable material. The material chosen need only enable the member to flex sufficiently enough so that a portion of the member can become disposed within the indent 418 when the distal tip member 414 is properly disposed, as described above. Examples of suitable materials for the flexible member include natural and synthetic rubbers, polymeric materials, and other flexible materials. In the illustrated embodiment, the proximal surface 456 comprises a substantially circular flexible member having a tapered outer portion 490.

In FIG. 10, the distal tip member 414 is fully retracted into the tubular member 412, and outer portion of the flexible member comprising the proximal surface 456 is deflected inward by the inner surface 422 of the tubular member 412. FIG. 11 illustrates the delivery system 410 disposed in the lumen 152 of a body vessel 150 with the distal tip member 414 in a fully extended configuration. In this configuration, the outer portion 490 of the flexible member comprising the proximal surface 456 has deflected into the indent 418 defined by the tubular member 412. The indent 418 engages the flexible member and retains a proximal portion of the distal tip member 414 within the tubular member 412. In this embodiment, the indent 418 advantageously comprises a circumferential indent 418 on the inner surface 422 of the tubular member 412. The circumferential nature of the indent 418 provides more surface for engaging the proximal surface 456 of the distal tip member 414. Other configurations can be used for the indent 418, including a partial circumferential indent and a plurality of partial circumferential indents.

The use of an indent 418 as the means for retaining a proximal portion of the distal tip member 414 within the tubular member 412 may be advantageous at least because it eliminates the need for a protrusion into the passageway 426 of the tubular member 412, such as that provided by the cap member 18 in the first exemplary embodiment. Any protrusion into the passageway 426 may introduce an obstacle into the path of an advancing self-expandable prosthetic device, which may require inward deflection to some degree by the prosthetic device during deployment. The use of the indent 418 substantially eliminates the need for any inward deflection of a prosthetic device during deployment.

Figure 12:
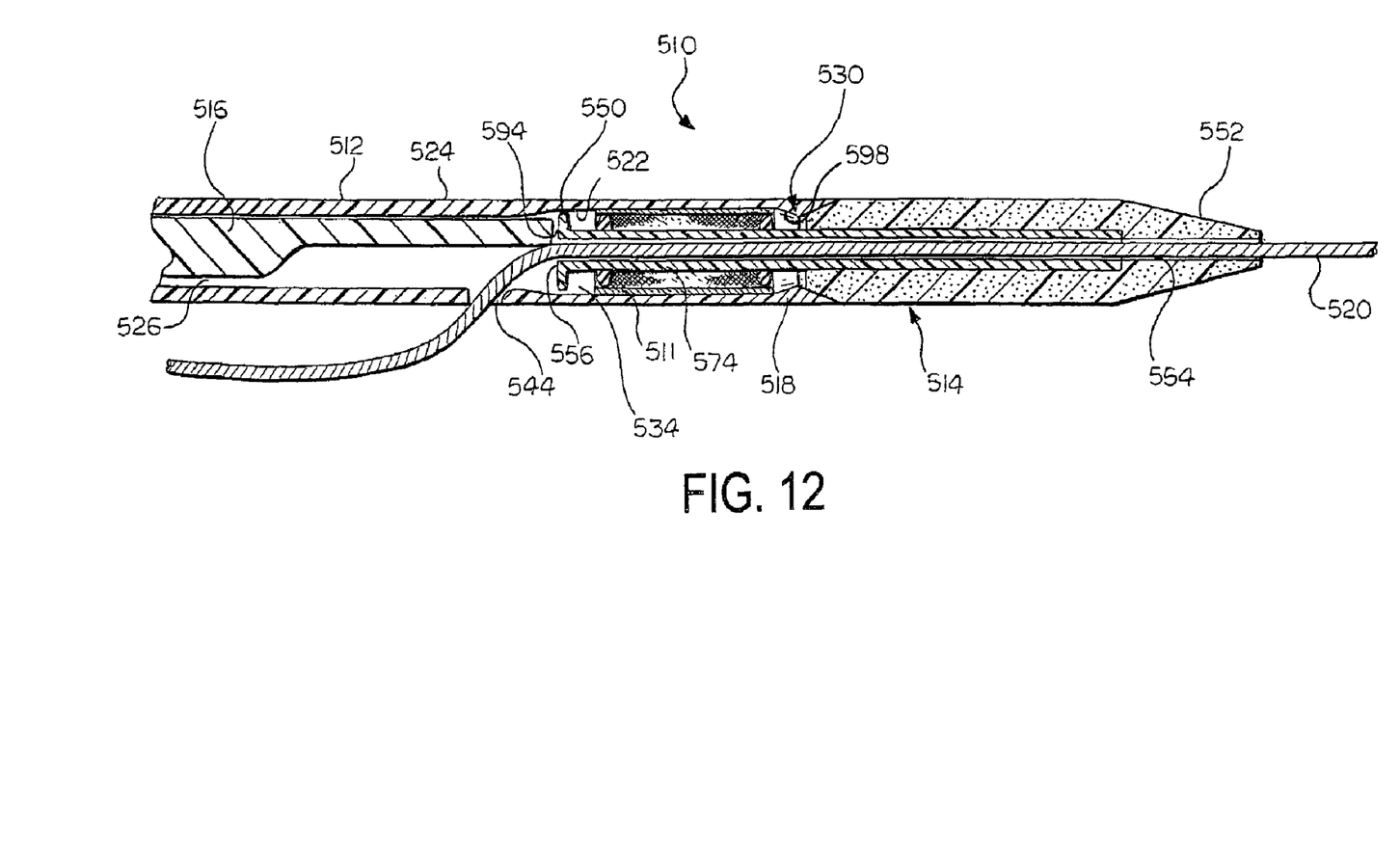
FIG. 12 is a sectional view of a delivery system according to a fifth exemplary embodiment of the invention.

FIG. 12 illustrates a delivery system 510 according to a fifth exemplary embodiment of the invention. The delivery system 510 of this embodiment is similar to the embodiment illustrated in FIGS. 1 through 4, except as indicated below. Accordingly, the delivery system 510 includes an elongate tubular member 512, a distal tip member 514, a pusher 516, and a means for retaining a proximal portion of the distal tip member 514 within the tubular member 512. In this embodiment, the means for retaining comprises a ramped projection 518 on the inner surface 522 of the tubular member 512.

The tubular member 512 has inner 522 and outer 524 surfaces and defines a passageway 526 extending from a proximal end (not illustrated in FIG. 12) to a distal end 530. The tubular member 512 defines a distal cavity 534 and an exchange port 544 through which a wireguide 520 can be passed.

The distal tip member 514 is a separate member from the tubular member 512, and has proximal 550 and distal 552 ends and defines a passageway 554 extending between the ends 550, 552. The passageway 554 can receive a portion of a wireguide 520. The distal tip member 514 defines a mounting region 574 on which an expandable prosthetic device 511 can be disposed.

The distal tip member 514 provides a proximal surface 556 at the proximal end 550 that is able to interact with a pushing surface 594 of the pusher 516. In this exemplary embodiment, the proximal surface 556 of the distal tip member 514 comprises a flange attached to the proximal end 550 of the distal tip member 514. The flange is a rigid section of material, such as plastic or metal. Alternatively, a pliable material can be used. Such materials may provide advantages in manufacturing the delivery system 510 by facilitating insertion of the distal tip member 514 into the tubular member 512.

The ramped projection 518 defines a ramp 598 extending into the passageway 526 of the tubular member 512. The height of the ramp 598 relative to the inner surface 522 of the tubular member 512 increases from the proximal side to the distal side of the ramp 518. The ramped projection 518 can comprise one or more discrete projections, or can comprise a circumferential projection. The ramped projection 518 allows a self-expandable prosthetic device to pass out of the distal end of the tubular member 512, while retaining a proximal portion of the distal tip member 514 within the tubular member 512.

Figure 13:
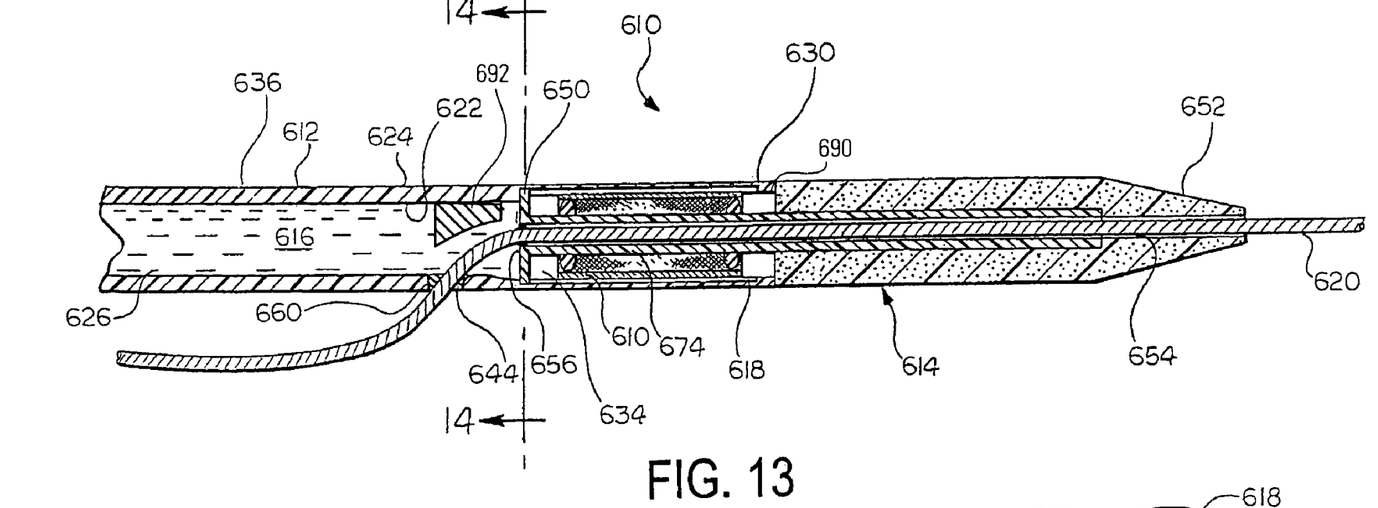
FIG. 13 is a sectional view of a delivery system according to a sixth exemplary embodiment of the invention.
Figure 14:
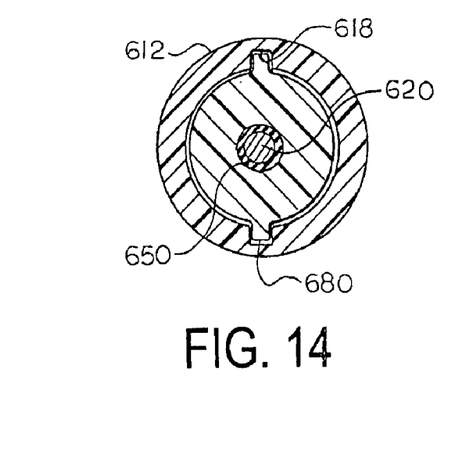
FIG. 14 is a magnified cross-sectional view of the delivery system illustrated in FIG. 13, taken along line 14-14.
Figure 15:
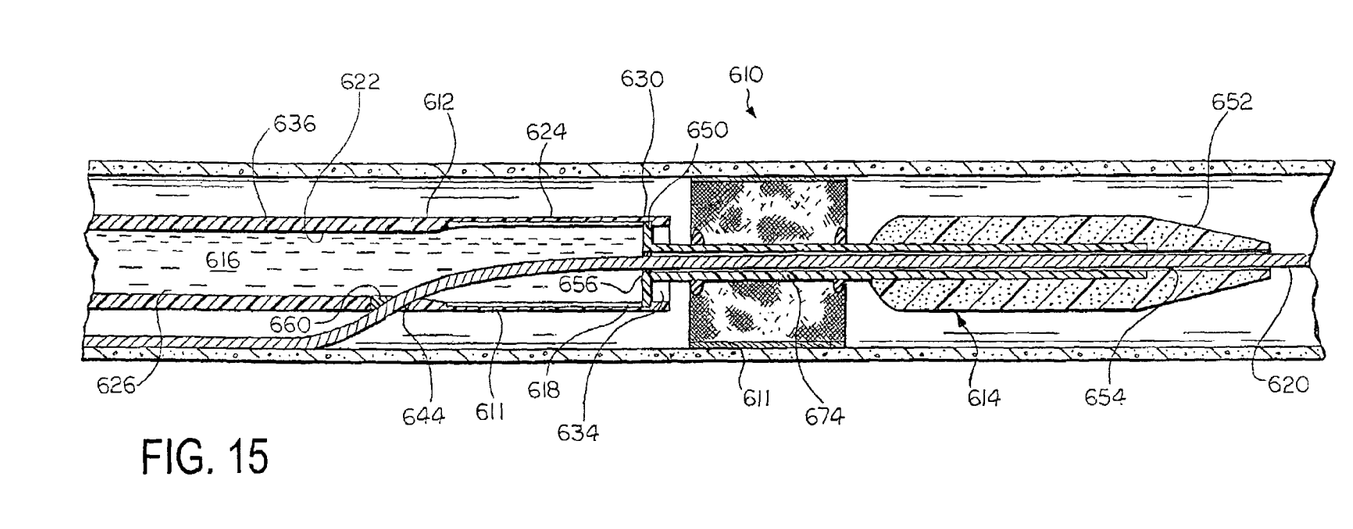
FIG. 15 is a sectioned partial view of a body vessel containing the delivery system illustrated in FIG. 13 disposed on a wireguide with an expandable prosthetic device in a fully deployed configuration.

FIGS. 13 through 15 illustrate a delivery system 610 according to a sixth exemplary embodiment of the invention. The delivery system 610 of this embodiment is similar to the embodiment illustrated in FIGS. 1 through 4, except as indicated below. Accordingly, the delivery system 610 includes an elongate tubular member 612, a distal tip member 614, and a means for retaining a proximal portion of the distal tip member 614 within the tubular member 612. In this embodiment, the means for retaining comprises a track 618 in the inner surface 622 of the tubular member 612. The track 618 extends from the proximal end (not illustrated in FIG. 13) toward the distal end 630 of the tubular member 612. Also, a fluid 616 is disposed in the passageway 626 of the tubular member 612.

The tubular member 612 has inner 622 and outer 624 surfaces and defines a passageway 626 extending from a proximal end (not illustrated in FIG. 13) to a distal end 630. The tubular member 612 defines a distal cavity 634 and an exchange port 644 through which a wireguide 620 can be passed. A seal 660 is disposed in the exchange port 644 and is adapted to prevent leakage of the fluid 616 from the passageway 626 while permitting passage of a wireguide 620 through the exchange port 644. A self-sealing rubber or polymeric member with one or more narrow slits can be used as the seal 660.

The track 618 comprises a recess in the inner surface 622 of the tubular member. The track 618 can have any suitable configuration, and need only be able to receive corresponding structural features of the distal tip member 614 as described below. The track 618 advantageously has a length that extends from a position distal to the distal side of the exchange port 644 to a position proximal to the distal end 630 of the tubular member 612. In the illustrated embodiment, the length of the track 618 is slightly greater than the length of the mounting region 674 of the distal tip member 614. This configuration permits the proximal surface 656 and mounting region 674, and therefore any mounted expandable prosthetic device 611, to travel a distance out of the distal end 630 of the tubular member 612 sufficient for full deployment. No matter the length, the track 618 should terminate proximal to the distal end 630 of the tubular member 612. The distal end of the track 618 can comprise a portion of the wall 636 of the tubular member 612, or can comprise a separate member disposed within the track 618. Also, as illustrated in FIG. 13 and described more fully below, a distal cap 690 can be used to terminate the track 618.

The inner surface 622 of the tubular member 612 can define any suitable number of tracks 618. The number chosen should correspond to the number of projections 680 on the proximal surface 656 of the distal tip member 614, as described below. In the exemplary embodiment, the inner surface 622 defines two tracks 618, and the proximal surface 656 of the distal tip member 614 includes two projections 680, each of which is disposed within a single track 618. The use of two or more tracks 618 and projections 680 may enhance the durability of the delivery system by providing multiple points of interaction between the elongate tubular member 612 and the distal tip member 614.

The distal tip member 614 is a separate member from the tubular member 612, and has proximal 650 and distal 662 ends and defines a passageway 654 extending between the ends 650, 662. The passageway 654 can receive a portion of a wireguide 620. The distal tip member 614 defines a mounting region 674 on which an expandable prosthetic device 611 can be disposed.

The distal tip member 614 provides a proximal surface 656 at the proximal end 650. The proximal surface 656 provides a surface against which the fluid 616 can exert a force to effect axial movement of the distal tip member 614. In this exemplary embodiment, the proximal surface 656 of the distal tip member 614 comprises a flange on the proximal end 650 of the distal tip member 614. The flange is a rigid section of material, such as plastic or metal. Also, the flange defines one or more projections 680 that are disposed within the track 618 of the tubular member 612. The flange defines an appropriate number of projections 680 based upon the number of tracks 618 in the inner surface 622 of the tubular member 612.

A distal cap 690 is positioned on the distal end 630 of the tubular member 612 and prevents escape of the distal tip member 614 from the tubular member 612. The distal cap 690 is advantageously snap-fit onto the distal end 630. This facilitates manufacturing by allowing the proximal end 650 to be disposed in the tubular member 612 and subsequently captured there by attachment of the distal cap 690. Of course, any other suitable connection can be used, including threaded connections, adhesives, welds, and the like.

In this embodiment, a fluid 616 is used to advance the distal tip member 614. FIG. 15 illustrates the delivery device 610 according to this embodiment with the distal tip member 614 in a fully advanced position. Pressure has been applied to the fluid 616, which in turn has placed pressure on the proximal surface 656 of the distal tip member 614. Pressure can be applied to the fluid 616 in any suitable manner, such as by introducing additional fluid into an opening at the proximal end of the tubular member 612 via a fluid delivery device, such as a syringe attached to the tubular member 612. Also, a bladder could be used with the tubular member 612, such as a bladder disposed within an opening in a wall of the tubular member 612. A positive pressure applied to the fluid will cause the distal tip member 614 to move axially in a distal direction. During this movement, the projections 680 move along and within the tracks 618, until the terminal ends of the tracks 618 is reached. At that point, which is illustrated in FIG. 15, the tracks 618 cooperate with the projections 680 to retain a proximal portion of the distal tip member 614 within the tubular member 612. A negative pressure could subsequently be applied to the fluid 612 to cause the distal tip member 614 to move axially in a proximal direction. That is, a vacuum can be pulled, such as with an attached syringe or similar device, to resheath the distal tip member 614.

The fluid 616 can comprise any suitable fluid, including liquids and gases. Saline and other biocompatible fluids are expected to be advantageous.

In embodiments that include a fluid 616, an indicia that correlates a known volume of the fluid 616 with an axial distance traveled by the distal tip member 614 could be included. For example, an attached syringe can include indicia that provide information relating to the axial movement of the distal tip member 614 relative to a particular volume of fluid 616 passed into the tubular member 612. The indicia can also be configured to provide information relative to the deployment state of a self-expandable prosthetic device disposed on the distal tip member 614.

A ramped surface 692 can be disposed on the inner surface of the tubular member 612 to aid in guidance of a wireguide 620 through the exchange port 644 and the passageway 654 of the distal tip member 614.

Figure 16:
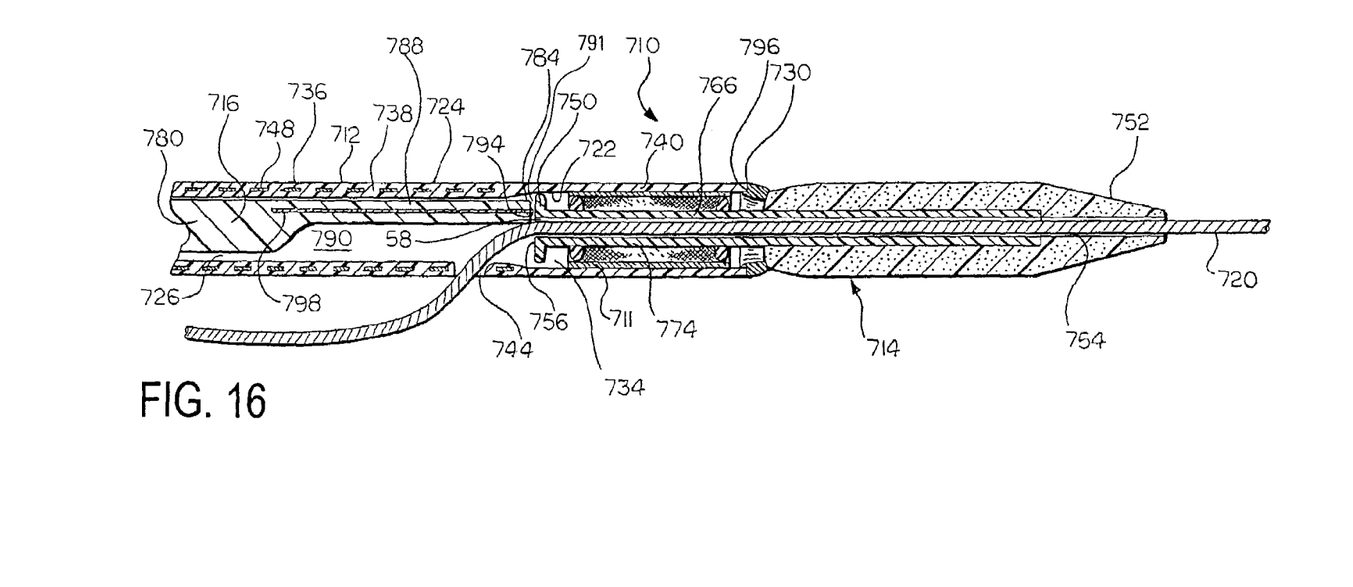
FIG. 16 is a sectional view of a delivery system according to a seventh exemplary embodiment of the invention.

FIG. 16 illustrates a delivery system 710 according to a seventh exemplary embodiment of the invention. The delivery system 710 of this embodiment is similar to the embodiment illustrated in FIGS. 1 through 4, except as indicated below. Accordingly, the delivery system 710 includes an elongate tubular member 712, a distal tip member 714, a pusher 716, and a means for retaining a proximal portion of the distal tip member 714 within the tubular member 712. In this embodiment, the means for retaining comprises a cap member 718 disposed on the tubular member 712. The cap member 718 of this embodiment is similar to the cap member 118 described above for the first exemplary embodiment.

Figure 17:
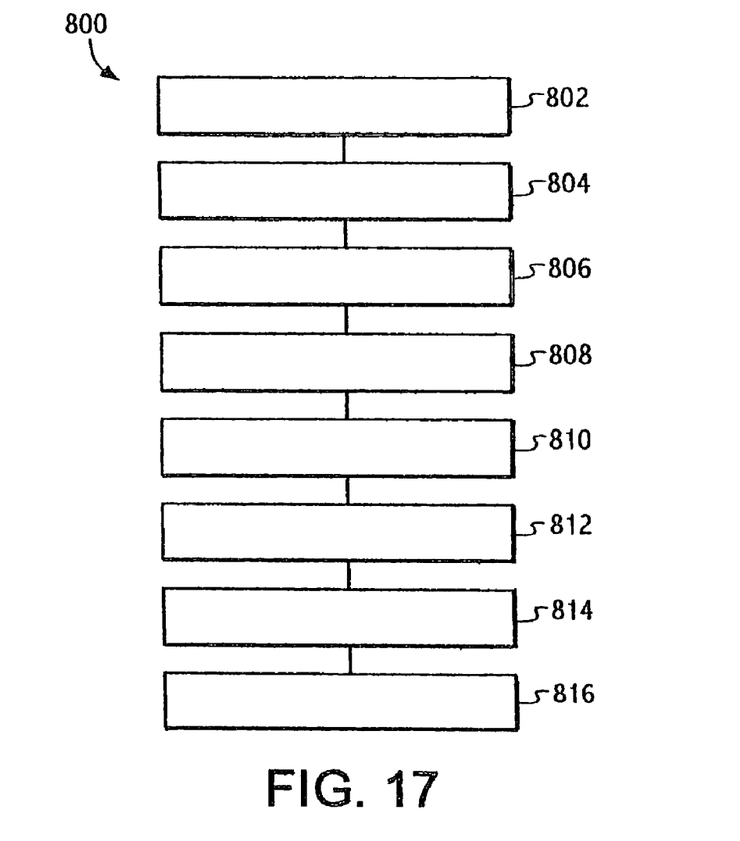
FIG. 17 is a flow diagram of a method of making a delivery system according to the invention.

The tubular member has inner 722 and outer 724 surfaces and defines a passageway 726 extending from a proximal end (not illustrated in FIG. 16) to a distal end 730. The passageway 726 includes a distal cavity 734 that receives a portion of the distal tip member 714. The tubular member also defines an exchange port 744 that comprises an opening through the wall 736 of the tubular member 712 and provides a communicative passageway between the passageway 726 defined by the tubular member 712 and the external environment of the tubular member 712. The tubular member 712 includes a reinforcing coil 748. The coil 748 can comprise a metal coil disposed on a surface of the tubular member 712 or embedded within the tubular member 712. The coil 748 provides a stiffening support to the tubular member 712 and may enhance the pushability and torqueability of the tubular member 712. In the illustrated embodiment, the tubular member 712 has a first wall portion 738, which has a first thickness, and a second wall portion 740, which has a second thickness. The first thickness is greater than the second thickness. The coil 748 can terminate proximal to the second portion 740 to allow for the reduced wall thickness in the second wall portion 740. Also, the coil 748 can terminate proximal to the exchange port 744 or, as illustrated in FIG. 17, the coil 748 can extend distally beyond the exchange port 744.

The distal tip member 714 is a separate member from the tubular member 712, and has proximal 750 and distal 752 ends and defines a passageway 754 extending between the ends 750, 752. The passageway 754 can receive a portion of a wireguide 720. The distal tip member 714 defines a mounting region 774 on which an expandable prosthetic device 711 can be disposed. The distal tip member 714 also provides a proximal surface 756 at the proximal end 750 that is able to interact with a pushing surface 794 of the pusher 716 to effect axial movement of the distal tip member 714.

The pusher 716 is an elongate member adapted to be substantially disposed within the passageway 726 of the tubular member 712. The pusher 716 comprises a main body 780 and has proximal (not illustrated in FIG. 16) and distal 784 ends. The pusher 716 of this embodiment includes a distal portion 788 having a width that is smaller than a width of a proximal portion. This reduced width at the distal portion 788 creates a void region 790 when the pusher 716 is disposed in the passageway 726 of the tubular member 712.

The distal end 784 of the pusher 716 defines a pushing surface 794 adapted to transfer a force generated by axial movement of the pusher 716 within the passageway 726 of the tubular member 712 onto the proximal surface 756 of the distal tip member 714.

In this embodiment, the pusher 716 includes a reinforcing member 798 in a distal portion 788 of the pusher 716. The reinforcing member 798 can be disposed on a surface of the pusher 716 or, as illustrated in FIG. 17, can be embedded within the material of the pusher 716. The reinforcing member 798 can comprise any suitable material, including plastic and metal, and can have any suitable size and configuration. The specific size and configuration chosen for the reinforcing member 798 for a particular embodiment of the invention will depend on several considerations, including the size and configuration of the distal portion 788 of the pusher 716. As illustrated in FIG. 16, the reinforcing member 798 advantageously has a length that extends proximally from a point within the distal portion 788 to a point within the portion having a width larger than that of the distal portion 788.

It is understood that features and/or components of all illustrated embodiments can be combined in any manner, despite the lack of any specific illustration and/or discussion of a particular combination, without departing from the spirit and scope of the invention. For example, a pusher can be attached to a proximal end of a distal tip member in any embodiment using any suitable means for attaching members. Also, a distal cap, such as a snap-fit cap member, can be attached to the distal end of a tubular member in any embodiment to provide a means for capturing the distal tip member and preventing its complete escape from the distal end of the tubular member.

Delivery devices according to the invention can be made using various manufacturing techniques. FIG. 17 is a flow diagram of a method 800 of making a delivery system according to the invention that includes a cap member as the means for retaining a proximal portion of the distal tip member within the tubular member, such as the embodiment illustrated in FIGS. 1 through 4. In one step 802, a distal tip member according to the invention is provided in a configuration that lacks a flange at the proximal end. In another step 804, a cap member according to the invention is provided. In another step 806, the cap member is passed over the proximal end of the distal tip member. In another step 808, a flange for attachment to the distal tip member is provided. In another step 810, the flange is attached to the proximal end of the distal tip member. In another step 812, a tubular member according to the invention is provided. In another step 814, the proximal end of the distal tip member is inserted into the passageway of the tubular member. In another step 816, the cap member is attached to the distal end of the tubular member.

The foregoing disclosure includes the best mode of the inventor for practicing the invention. It is apparent, however, that those skilled in the relevant art will recognize variations of the invention that are not described herein. While the invention is defined by the appended claims, the invention is not limited to the literal meaning of the claims, but also includes these variations.

We claim:

1. A delivery system for placing a self-expandable prosthetic device within a body vessel, said delivery system comprising:
    an elongate tubular member comprising a circumferential wall and having first proximal and distal ends, the elongate tubular member defining a first passageway extending between the first proximal and distal ends and an exchange port extending through the wall and providing access to the first passageway;
    a distal tip member having second proximal and distal ends, defining a second passageway extending between the second proximal and distal ends, and defining a mounting region about which said self-expandable prosthetic device can be disposed, the second proximal end defining a proximal surface and being slideably disposed within the first passageway;
    a pusher disposed within the first passageway and comprising a third distal end adapted to interact with the proximal surface of the distal tip member; and
    means for retaining the second proximal end of the distal tip member within the first passageway;
    wherein the second proximal end of the distal tip member defines a projection directed radially outward;
    wherein the means for retaining the second proximal end of the distal tip member within the first passageway comprises a track defined by the wall of the elongate tubular member, wherein the track terminates proximal to the distal end of the elongate tubular member; and
    wherein the projection is slideably disposed within the track;
    wherein the second proximal end of the distal tip member further defines a second projection directed radially outward;
    wherein the means for retaining the second proximal end of the distal tip member within the first passageway further comprises a second track defined by the wall of the elongate tubular member, wherein the second track terminates proximal to the distal end of the elongate tubular member; and
    wherein the second projection is slideably disposed within the second track.

2. A delivery system according to claim 1, wherein a distal portion of the first passageway defines a cavity that receives the second proximal end of the distal tip member.

3. A delivery system according to claim 2, wherein the elongate tubular member has a first inner diameter at an axial position within the length of the cavity and a second inner diameter at an axial position that is not within the length of the cavity.

4. A delivery system according to claim 3, wherein the first inner diameter is greater than the second inner diameter.

5. A delivery system according to claim 1, wherein the distal tip member comprises a taper at the second distal end.

6. A delivery system according to claim 1, wherein the distal tip member includes a portion having an outer diameter that is greater than an inner diameter of the elongate tubular member at the first distal end.

7. A delivery system according to claim 1 wherein the distal tip member comprises a tip body disposed on a tubular member defining the second passageway.

8. A delivery system according to claim 7, wherein the tip body is formed of a flexible polymeric material or a gel.

9. A delivery system according to claim 1, wherein the pusher includes first and second axial portions, the first axial portion having a first diameter and the second axial portion having a second, different diameter.

10. A delivery system according to claim 9, wherein the first axial portion includes the third distal end of the pusher, and wherein the first diameter is less than the second, different diameter.

11. A delivery system according to claim 10, wherein the elongate tubular member defines a projection extending into the first passageway of the elongate tubular member.

12. A delivery system according to claim 11, wherein the pusher includes a transition portion having a diameter that varies from the first diameter to the second diameter, the transition portion defining a transition surface; and
    wherein the projection defined by the elongate tubular member is substantially complimentary to the transition surface.

13. A delivery system according to claim 1, wherein the elongate tubular member includes a reinforcing coil disposed in the wall.

* * * * *